(12) United States Patent
Nadkarni et al.

(10) Patent No.: US 9,364,518 B2
(45) Date of Patent: Jun. 14, 2016

(54) PHARMACEUTICAL COMPOSITION CONTAINING GOSERELIN FOR IN-SITU IMPLANT

(75) Inventors: Sunil S. Nadkarni, Bhat (IN); Jaya Abraham, Bhat (IN); Amit Kesarwani, Bhat (IN); Astha Parmar, Bhat (IN)

(73) Assignee: Torrent Pharmaceuticals Limited, Ahmedabad, Gujarat (IN)

( * ) Notice: Subject to any disclaimer, the term of this patent is extended or adjusted under 35 U.S.C. 154(b) by 0 days.

(21) Appl. No.: 13/805,624

(22) PCT Filed: Jun. 24, 2011

(86) PCT No.: PCT/IB2011/001449
§ 371 (c)(1),
(2), (4) Date: Mar. 6, 2013

(87) PCT Pub. No.: WO2011/161531
PCT Pub. Date: Dec. 29, 2011

(65) Prior Publication Data
US 2013/0157951 A1 Jun. 20, 2013

(30) Foreign Application Priority Data
Jun. 24, 2010 (IN) .......................... 1863/MUM/2010

(51) Int. Cl.
*A61K 38/25* (2006.01)
*A61K 9/00* (2006.01)
*A61K 47/34* (2006.01)
*A61K 38/09* (2006.01)

(52) U.S. Cl.
CPC ............... *A61K 38/25* (2013.01); *A61K 9/0024* (2013.01); *A61K 38/09* (2013.01); *A61K 47/34* (2013.01)

(58) Field of Classification Search
None
See application file for complete search history.

(56) References Cited

U.S. PATENT DOCUMENTS

| 5,366,734 | A | 11/1994 | Hutchinson | |
|---|---|---|---|---|
| 6,565,874 | B1 * | 5/2003 | Dunn et al. | 424/426 |
| 2006/0074027 | A1 * | 4/2006 | Saito | A61K 9/5031 424/468 |
| 2007/0104759 | A1 | 5/2007 | Dunn | |
| 2007/0196416 | A1 * | 8/2007 | Li et al. | 424/422 |
| 2010/0189763 | A1 * | 7/2010 | Nettles | 424/426 |

FOREIGN PATENT DOCUMENTS

| WO | WO 98/27963 | * | 7/1998 | ............... A61K 9/00 |
|---|---|---|---|---|
| WO | WO 02/49573 | | 6/2002 | |
| WO | WO0249573 | * | 6/2002 | ............... A61K 9/00 |

OTHER PUBLICATIONS

Goserlin versus leuprolide before hysterectomy for uterine fibroids, Intl. Jl. of Gyn. and Obst., 101, 178-183 (2008).*
Luan, X, et al. "Influence of the poly(lactide-co-glycolide) type on the leuprolide release from in-situ forming microparticle systems" *Jr. Controlled Release* 110(2):266-272 (2006).
Packhaeuser, C.B. et al."In-Situ Forming Parenteral Drug Delivery Systems: An Overview" *European Journal of Pharmaceutics and Biopharmaceutics* 58(2):445-455 (2004).
International Search Report from corresponding application PCT/IB2011/001449 mailed Oct. 25, 2011.
Prescribing Information for ELIGARD® (leuprolide acetate) suspension for subcutaneous injection (Feb. 27, 2013).
Prescribing Information for ZOLADEX® (goserelin acetate implant) (Jun. 18, 2013).
Eligard® product monograph—Canada (May 31, 2011).
Goserelin (http://www.drugs.com/mmx/goserelin-acetate.html), last accessed on Jun. 16, 2014.
Leuprolide (http://www.drugs.com/ppa/leuprolide-acetate.html), last accessed on Jun. 16, 2014.
Plosker et al. Drugs (1994) 48(6): 930-967.
Perry et al. Drugs (1996) 51(2): 319-346.
Boehringer Ingelheim memo entitled N02-06: Molecular Weight of RESOMER®, dated Apr. 7, 2006.
Webpage printout related to Biodegradable Polymers (PLA•PLGA) published by Wako Pure Chemical Industries, Ltd., dated Oct. 10, 2015.
Certificate of Analysis for a PLGA (PURASORB® PDLG 5002A), dated Sep. 11, 2009.

* cited by examiner

*Primary Examiner* — Satyanarayana R Gudibande
*Assistant Examiner* — Joseph Fischer
(74) *Attorney, Agent, or Firm* — Melissa M. Hayworth; Daniel R. Evans

(57) ABSTRACT

The present invention provides a pharmaceutical composition capable of forming in-situ implant comprising goserelin or its pharmaceutically acceptable salts thereof, biodegradable polymer and a biocompatible organic solvent wherein the biocompatible organic solvent is miscible to dispersible in aqueous medium or body fluid. The present invention further provides a process for the preparation of pharmaceutical composition capable of forming in-situ implant. A kit containing composition for in-situ implant is provided comprising a first vial comprising a composition comprising a biodegradable polymer and a biocompatible organic solvent; wherein the biocompatible organic solvent is miscible to dispersible in aqueous medium or body fluid; and a second vial comprising goserelin acetate.

20 Claims, 1 Drawing Sheet

PHARMACEUTICAL COMPOSITION CONTAINING GOSERELIN FOR IN-SITU IMPLANT

FIELD OF THE INVENTION

This invention relates to pharmaceutical composition capable of forming in-situ implant, which comprises goserelin or its pharmaceutically acceptable salts, biodegradable polymer and a biocompatible organic solvent. Such implant formed in-situ, releases the drug in the body for prolonged period of time. Present invention also relates to a process for preparing said composition.

BACKGROUND

Goserelin is a synthetic decapeptide analogue of luteinizing hormone-releasing hormone (LHRH), also known as gonadotropin releasing hormone (GnRH) agonist analogue. On chronic administration Goserelin results in inhibition of pituitary luteinizing hormone secretion leading to a fall in serum testosterone concentrations in males and serum estradiol concentrations in females.

Goserelin is indicated in the palliative treatment of advanced carcinoma of the prostate as well as endometriosis. Goserelin has been approved in USA since 1989 as ZOLADEX® implant for subcutaneous implantation and is marketed by Astra Zeneca in the USA. It is available as ZOLADEX® 10.8 mg implant containing goserelin acetate equivalent to 10.8 mg of goserelin, designed for subcutaneous implantation with continuous release over a 12-week period and as ZOLADEX® 3.6 mg implant containing goserelin acetate equivalent to 3.6 mg of goserelin, designed for subcutaneous implantation with continuous release over a 28-day period.

ZOLADEX® is a 1 to 1.5 mm diameter cylinder, preloaded in a special single-use syringe with a 14-gauge to 16-gauge hypodermic needle. The main disadvantage related with ZOLADEX® is that it causes severe pain and haematomas when implanted into the patient. Hence, patient friendly mode of administration is not only desirable attribute but would also improve compliance to therapy.

U.S. Pat. No. 5,366,734 discloses the solid implant formulation of peptide and U.S. Pat. No. 5,004,602 discloses process for the preparation of such solid implant using melt extrusion in which freeze dried drug (peptide) and polymer has been extruded together under pressure at 70° C. to form a rod, from which implants of the required weight has been obtained. WO9324150 discloses composition in the form of microparticles or an implant containing salt of peptide with the polymer having carboxyl terminal group. U.S. Pat. No. 6,620,422 discloses dispersion of drug dispersed into polymer and use of such particles for the preparation of implant. During implant preparation, peptides and proteins are exposed to various unfavorable conditions. The exposure to high temperatures, shear forces, or high pressures may cause protein unfolding and irreversible aggregation. Further, complex manufacturing process for the solid implant by melt extrusion or injection moulding is difficult and requires tight process controls.

Various options have been explored to deliver controlled release goserelin such as microspheres, microparticles, nanoparticles etc, but production of microspheres is complex multiple step process involving optimization and control on many critical process parameters and high process loss add to the overall cost of the product.

Alternative approaches have been developed to overcome the shortcomings of solid implant, particularly pain at site of injection. U.S. Pat. No. 4,938,763 discloses method of forming in-situ implant containing biodegradable water insoluble polymer and biocompatible water soluble solvent. U.S. Pat. No. 5,077,049 discloses in-situ implant preparation containing biodegradable water insoluble polymer and biocompatible water soluble solvent for the periodontal pocket. U.S. Pat. No. 6,565,874 and U.S. Pat. No. 6,773,714 disclose in-situ implant composition of leuprolide acetate. US20040010224 discloses kits for the preparation of an in-situ implant composition containing biodegradable polymer and biocompatible solvents.

However, it has been found that the formed in-situ implants by above technologies, gives initial burst release and hence it is difficult to maintain constant plasma drug concentration throughout treatment regimen. Further, if the active agent is particularly toxic, this initial burst release of the active agent is likely to lead to increased incidences and magnitude of adverse drug reactions. To reduce this initial burst release various approaches have been developed by the scientists. For example, U.S. Pat. No. 5,702,716 discloses use of the rate-retarding agents such as ester of a mono, di or tricarboxylic acid, a polyhydroxy alcohol, a fatty acid, a fatty acid ester, an epoxidized oil, a sterol to retards the rate of release of the biologically active agent from the matrix. U.S. Pat. No. 5,744,153 discloses incorporation of drug into microstructures, such as liposphere, liposomes, microcapsules, microparticles, and nanoparticles followed by suspending such drug containing microstructure into liquid implant forming composition. U.S. Pat. No. 6,630,155 discloses use of poly (lactide-co-glycolide)/polyethylene glycol (PLG/PEG) block copolymer to reduce the initial burst of biologically active agent released from the polymeric composition as it solidifies to form the solid implant upon administration. WO2005067889 discloses controlled release device comprising biodegradable polymer system of copolymers and polymeric blends comprising a hydrophobic component and a hydrophilic component to reduce burst effect or lag period. WO2008008363 discloses method of conjugating peptide with lipophilic moiety to reduce the initial burst release.

Applicant is unaware about any prior arts, which discloses pharmaceutical composition for the preparation of in-situ implant of goserelin which overcomes the above cited problems such as initial burst release. Moreover prior art uses complex & costly process, particularly the sterilization procedure is carried out using gamma-irradiation which has implications on polymer stability. Inventors of the present invention have surprisingly found the pharmaceutical composition of goserelin for the preparation of in-situ implant, which overcomes the above cited problems. Additionally, inventors have also discovered simpler and more efficient process for the preparation of the goserelin in-situ implant.

SUMMARY OF THE INVENTION

The first embodiment of the present invention is to provide pharmaceutical composition capable of forming in-situ implant comprising goserelin or its pharmaceutically acceptable salts thereof, biodegradable polymer and a biocompatible organic solvent which is miscible to dispersible in aqueous medium or body fluid.

The first embodiment of the present invention is to provide pharmaceutical composition capable of forming in-situ implant comprising goserelin or its pharmaceutically acceptable salts thereof, biodegradable polymer and a biocompatible organic solvent which is miscible to dispersible in aqueous medium or body fluid, characterized in that the biodegradable polymer is aseptically dried either by lyophilization or spray drying prior to the mixing it with biocompatible organic solvent.

An another embodiment of the present invention is to provide pharmaceutical composition capable of forming in-situ implant comprising goserelin acetate, biodegradable polymer and a biocompatible organic solvent which is miscible to dispersible in aqueous medium or body fluid.

An another embodiment of the present invention is to provide pharmaceutical composition capable of forming in-situ implant comprising goserelin pamoate, biodegradable polymer and a biocompatible organic solvent which is miscible to dispersible in aqueous medium or body fluid.

An another embodiment of the present invention is to provide pharmaceutical composition capable of forming in-situ implant comprising goserelin acetate, biodegradable polymer which is PLGA (lactic acid and glycolic acid copolymer) and a biocompatible organic solvent which is miscible to dispersible in aqueous medium or body fluid.

An another embodiment of the present invention is to provide pharmaceutical composition capable of forming in-situ implant comprising goserelin acetate, biodegradable polymer which is PLGA (lactic acid and glycolic acid copolymer) and a biocompatible organic solvent which is miscible to dispersible in aqueous medium or body fluid; wherein the composition exhibits minimal burst.

An another embodiment of the present invention is to provide pharmaceutical composition capable of forming in-situ implant comprising goserelin acetate, PLGA (lactic acid and glycolic acid copolymer) which is carboxyl terminated or ester terminated and a biocompatible organic solvent which is miscible to dispersible in aqueous medium or body fluid.

An another embodiment of the present invention is to provide pharmaceutical composition capable of forming in-situ implant comprising goserelin acetate, PLGA (lactic acid and glycolic acid copolymer) which is carboxyl terminated and a biocompatible organic solvent which is miscible to dispersible in aqueous medium or body fluid.

An another embodiment of the present invention is to provide pharmaceutical composition capable of forming in-situ implant comprising goserelin acetate, PLGA (lactic acid and glycolic acid copolymer) and N-methyl-2-pyrrolidone (NMP).

An another embodiment of the present invention is to provide pharmaceutical composition capable of forming in-situ implant comprising goserelin acetate, PLGA (lactic acid and glycolic acid copolymer) which is carboxyl terminated and N-methyl-2-pyrrolidone (NMP).

An another embodiment of the present invention is to provide pharmaceutical composition capable of forming in-situ implant comprising goserelin acetate, PLGA (lactic acid and glycolic acid copolymer) which is carboxyl terminated and a mixture of solvent comprises N-methyl-2-pyrrolidone (NMP) and at least one another solvent.

An another embodiment of the present invention is to provide pharmaceutical composition capable of forming in-situ implant comprising goserelin acetate, PLGA (lactic acid and glycolic acid copolymer) which is carboxyl terminated and a mixture of solvent comprises N-methyl-2-pyrrolidone (NMP) and benzyl benzoate.

An another embodiment of the present invention is to provide pharmaceutical composition capable of forming in-situ implant comprising goserelin acetate, mixture of PLGA and at least one another biodegradable polymer, and a biocompatible organic solvent which is miscible to dispersible in aqueous medium or body fluid, preferably N-methyl-2-pyrrolidone (NMP).

An another embodiment of the present invention is to provide pharmaceutical composition capable of forming in-situ implant comprising goserelin acetate, mixture of biodegradable polymer comprising PLGA, and N-methyl-2-pyrrolidone (NMP).

An another embodiment of the present invention is to provide pharmaceutical composition capable of forming in-situ implant comprising goserelin acetate, mixture of biodegradable polymer comprising PLGA, and a biocompatible organic solvent comprising mixture N-methyl-2-pyrrolidone (NMP) and at least one another solvent.

An another embodiment of the present invention is to provide pharmaceutical composition capable of forming in-situ implant comprising goserelin acetate, PLGA (lactic acid and glycolic acid copolymer) and a biocompatible organic solvent comprising mixture N-methyl-2-pyrrolidone (NMP) and at least one another solvent.

In another embodiment, present invention provides pharmaceutical composition capable of forming in-situ implant comprising goserelin acetate which is in the range of about 0.5% to about 5% by weight of the composition, biodegradable polymer which is in the range of about 20% to about 80%, preferably in the range of about 30% to about 50% by weight of the composition and biocompatible organic solvent in the range of about 20% to about 80% by weight of the composition, preferably in the range of about 50% to about 70% by weight of the composition.

In another embodiment, present invention provides pharmaceutical composition capable of forming in-situ implant comprising goserelin acetate, PLGA comprising different ratio of lactic acid to glycolic acid, such as 85:15 PLGA, 75:25 PLGA, 70:30 PLGA, 65:35 PLGA and 50:50 PLGA and the mixture thereof and biocompatible organic solvent.

In another embodiment, present invention provides a method to suppress the serum testosterone level with a pharmaceutical composition capable of forming in-situ implant comprising goserelin acetate.

In another embodiment, present invention provides a pharmaceutical composition capable of forming in-situ implant comprising goserelin acetate to suppress the serum testosterone level.

In another embodiment, present invention provides a process for the preparation of composition capable of forming in-situ implant comprising:
1. Preparing goserelin solution in a suitable solvent, sterilizing the solution by suitable technique and subsequent lyophilizing in a suitable container closure system;
2. Mixing biodegradable polymer and biocompatible organic solvent and sterilized into a suitable container closure system by suitable technique or aseptically mixed after sterilizing separately and filled into a suitable container closure system.

In another embodiment, present invention provides a process for the preparation of composition capable of forming in-situ implant comprising:
1. Preparing goserelin solution in a suitable solvent, sterilizing the solution by membrane filtration and subsequent lyophilizing in a suitable container closure system;
2. Mixing biodegradable polymer and biocompatible organic solvent and sterilized into a suitable container closure system by suitable technique or aseptically mixed after sterilizing separately and filled into a suitable container closure system.

In another embodiment, present invention provides a process for the preparation of composition capable of forming in-situ implant comprising:

1. Preparing goserelin acetate solution in a suitable solvent followed by sterilizing it by membrane filtration and subsequent lyophilizing in a suitable container closure system;
2. Dissolving biodegradable polymer in a suitable solvent and sterilizing by suitable technique and lyophilizing in bulk;
3. Sterilizing biocompatible organic solvent separately by suitable technique;
4. Mixing polymer and solvent of step 2 & 3 aseptically and filling in a suitable container closure system.

In another embodiment, present invention provides a process for the preparation of composition capable of forming in-situ implant comprising:
1. Preparing goserelin acetate solution in a suitable solvent followed by sterilizing it by membrane filtration and subsequent lyophilizing in a suitable container closure system;
2. Dissolving biodegradable polymer in a suitable solvent and sterilizing by suitable technique and drying aseptically by spray drying;
3. Sterilizing biocompatible organic solvent separately by suitable technique;
4. Mixing polymer and solvent of step 2 & 3 aseptically and filling in a suitable container closure system.

In another embodiment, present invention provides a process for the preparation of composition capable of forming in-situ implant comprising:
1. Preparing goserelin acetate solution in a suitable solvent followed by sterilizing it by membrane filtration and subsequent lyophilizing in a suitable container closure system;
2. Dissolving biodegradable polymer in a suitable solvent and sterilizing by membrane filtration technique and lyophilized in bulk;
3. Sterilizing biocompatible organic solvent separately by membrane filtration technique;
4. Mixing polymer and solvent of step 2 & 3 aseptically and filling in a suitable container closure system.

In another embodiment, present invention provides a process for the preparation of composition capable of forming in-situ implant comprising:
1. Preparing solution of goserelin acetate and biodegradable polymer in a suitable solvent followed by sterilizing it by membrane filtration and subsequent lyophilizing in a suitable container closure system;
2. Dissolving remaining biodegradable polymer in a suitable solvent and sterilizing by suitable technique and lyophilized;
3. Sterilizing biocompatible organic solvent separately by suitable technique;
4. Mixing polymer and solvent of step 2 & 3 aseptically and filling in a suitable container closure system.

In another embodiment, present invention provides a process for the preparation of composition capable of forming in-situ implant comprising:
1. Preparing goserelin acetate solution in a suitable solvent followed by sterilizing it by membrane filtration and subsequent lyophilizing in a suitable container closure system in which primary drying is performed above glass transition temperature of the goserelin acetate solution;
2. Dissolving biodegradable polymer in a suitable solvent and sterilizing by membrane filtration technique and lyophilized in bulk;
3. Sterilizing biocompatible organic solvent separately by membrane filtration technique;
4. Mixing polymer and solvent of step 2 & 3 aseptically and filling in a suitable container closure system.

In another embodiment, present invention provides a process for the preparation of composition capable of forming in-situ implant comprising:
1. Preparing goserelin acetate solution in a suitable solvent followed by sterilizing it by membrane filtration and subsequent lyophilizing in a suitable container closure system in which primary drying is performed above glass transition temperature of the goserelin acetate solution;
2. Dissolving biodegradable polymer in a suitable solvent and sterilizing by membrane filtration technique and lyophilizing in bulk;
3. Biocompatible organic solvent containing strong acid is sterilized separately by membrane filtration technique;
4. Aseptically mixing polymer and solvent obtained in step 2 & 3 and filling in a suitable container closure system.

In another embodiment, present invention provides method for administration of the composition into the mammal for treatment of the prostate cancer, endometriosis, as an endometrial-thinning agent prior to endometrial ablation for dysfunctional uterine bleeding, and in the palliative treatment of advanced breast cancer in pre- and perimenopausal women.

DEFINITIONS

As used herein, the phrase "in-situ implant" is used to indicate that gel or semisolid or solid implant structure is formed when a pharmaceutical composition is placed into a mammalian body and is intended to remain at the site of administration and release the drug for a period of several weeks or more in the mammalian body.

As used herein, the phrase "a prolonged period of time" shall have different meanings with respect to the various drug delivery systems and its application. Normally, it includes one hour or higher, up to one year or more. In accordance with the present invention, the meaning of the phrase "a prolonged period of time" is defined as release of active agent for the time up to one week or up to six months.

The phrase "pharmaceutically acceptable salt" is defined as the salts of goserelin suitable for use in the treatment of mammals without undue toxicity, irritation, allergic response and the like except that is exerted by the goserelin. Preferable pharmaceutical salts for present invention are acetate, pamoate or mesylate salt of goserelin.

In the present invention, the term "biodegradable" refers to a material that gradually decomposes, dissolves, hydrolyzes and/or erodes in vivo. Generally, the "biodegradable polymers" herein are polymers that are hydrolysable, and/or bio-erodable in-situ primarily through hydrolysis and/or enzymolysis. The term "biodegradable polymer" as used herein is meant to include any biocompatible and/or biodegradable synthetic and natural polymers that can be used in vivo.

The phrase "biocompatible organic solvent" is defined here as the organic solvent generally does not react or, cause any untoward interaction with the biological tissues.

The phrase "Pharmaceutical composition capable of forming in-situ implant" is defined here for the pharmaceutical composition which forms gel or semisolid or solid implant upon administration in-vivo upon contact with body fluids.

"Polydispersity Index (PDI)" is defined here as a measure of the distribution of molecular mass in a given polymer sample. The PDI calculated is the weight average molecular weight divided by the number average molecular weight. It indicates the distribution of individual molecular masses in a batch of polymers. Weight average molecular weight of a polymer material or fraction of a polymer material describes an average property derived from the individual molecular weights of all the individual polymer molecules making up the material or fraction. For any given weight average molecular weight that a polymer material or fraction may have there are many possible distributions of individual molecular weights of the molecules making up the material or fraction.

$$PDI = Mw/Mn$$

Mn is more sensitive to molecules of low molecular mass, while Mw is more sensitive to molecules of high molecular mass. Gamma rays are known to induce structural changes through scission and crosslinking. PDI after gamma irradiation of polymer solution is increased which indicates broad molecular weight distribution.

The use of the terms "a" and "an" and "the" and similar referents in the context of describing the invention are to be construed to cover both the singular and the plural, unless otherwise indicated herein or clearly contradicted by context.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

The term "Burst" as used herein denotes undesirable increase in the release of goserelin in first 24-48 hours after administration of pharmaceutical composition of present invention The phrase "Suitable container" as used herein refers to container for holding unit or multiple dose of sterile liquid or carrying out lyophilization and holding lyophilized product. The "suitable container" as referred herein is compatible with the drug product as characterized by physical and chemical stability and low leach ability. The suitable container can be vial or syringe and material of construction range from glass to elastomeric material. The inner surface of container can be uncoated or coated with silicon or any other hydrophobic material.

The phrase "Suitable container closure system" as referred herein comprises of "suitable container" as defined above and closure to seal the container. It can be a elastomeric cap for vials or plunger for vial. The closure can be uncoated or coated with inert material like Teflon (PTFE).

The term "Burst Index" as used herein is a measure to determine the reduction in burst effect and is calculated here as a ratio of maximal plasma concentration observed in-vivo in the first 24 hour after implant administration between different formulations.

The term "Mammal" as used herein means warm blooded animals, that can be human or non human (mice, rat, guinea pig, rabbit, dog), preferably human.

DETAIL DESCRIPTION OF THE INVENTION

Figure 1:
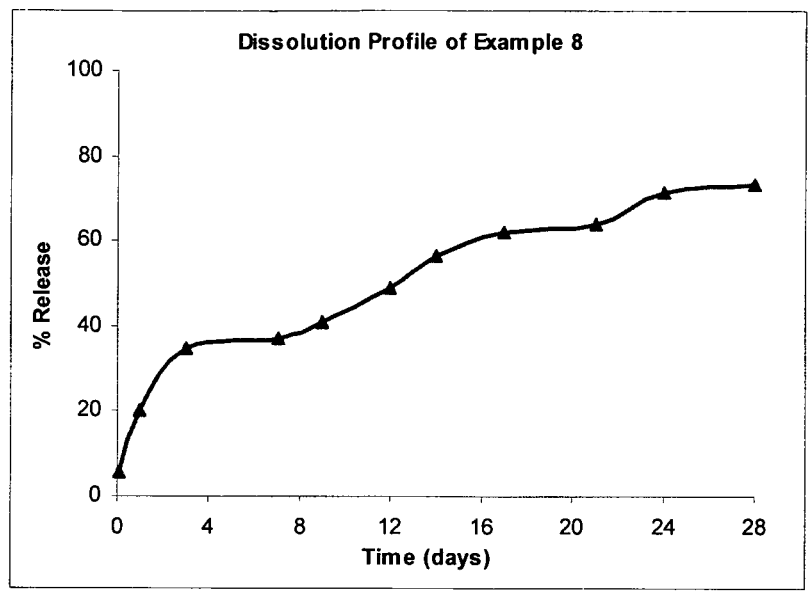
FIG. 1—Dissolution profile of Example 8
FIG. 2—In vitro release profile of Example 11
Figure 2:
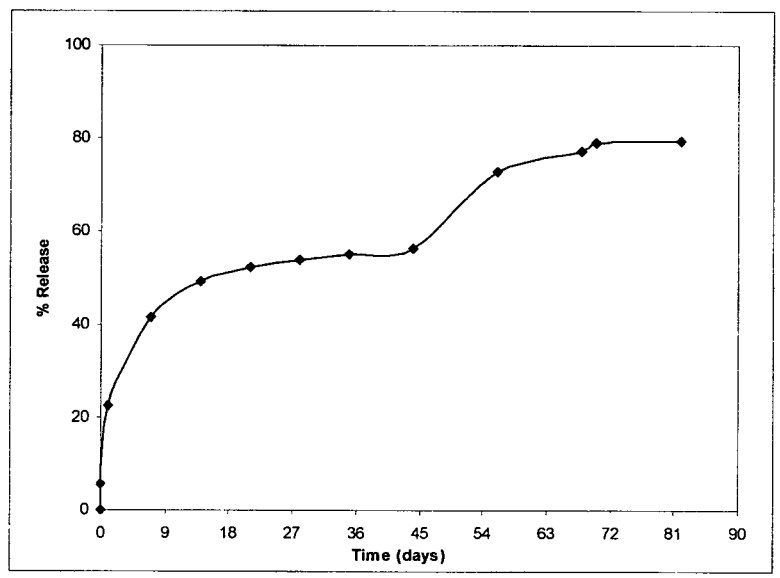

The present invention provides a pharmaceutical composition capable of forming in-situ implant, which releases the drug in a body for a prolonged period of time. The composition includes goserelin or its pharmaceutically acceptable salts, biodegradable polymer and a biocompatible organic solvent wherein the biocompatible organic solvent is miscible to dispersible in aqueous medium or body fluid. The present invention also provides method of preparation of such pharmaceutical composition capable of forming in-situ implant.

In the present invention, goserelin can be used in any suitable salts, which can be incorporated in the present composition to provide the drug release for a prolonged period of time. The preferred salt of the present invention is goserelin acetate. However the invention is not limited to acetate salt, other pharmaceutically acceptable salts of goserelin such as pamoate and mesylate can also be employed.

The composition is formulated as a subcutaneous/intra muscular/intra peritoneal injection for administration about once per month, about once per two months, about once per three months, or about once per four months to about once per six months. Preferably, the composition is a liquid or a gel composition, suitable for injection into a patient.

Further, in the invention, suitable biodegradable polymer and biocompatible organic solvent can be selected based on the results of the experiments, along with further optimization of the formulation by evaluating effect on drug release from the formulation in-vitro and in-vivo and an effect on the storage stability.

Any biodegradable polymer, which is suitable for present invention can be used. Some non-limiting examples of the polymers are polylactides, polyglycolides, polycaprolactones, polydioxannones, polycarbonates, polyhydroxybutyrates, polyalkyene oxalates, polyanhydrides, polyamides, polyesteramides, polyurethanes, polyacetals, polyketals, polyorthocarbonates, polyphosphazenes, polyhydroxyvalerates, polyalkylene succinates, poly(malic acid), poly(amino acids), chitin, chitosan, polyorthoesters, and copolymers, polyethylene-polypropylene glycol, block polymer of polylactides-glycolides with polyethyleneglycol, terpolymers, block copolymers, branched copolymers, and mixtures thereof. In the present invention, preferred biodegradable polymers are polylactides, polyglycolides, copolymer of lactic acid and glycolic acid, polycaprolactones, or their mixtures thereof. More preferred biodegradable polymer is copolymer of lactic acid and glycolic acid (PLGA). Commercially available PLGAs are RESOMER® (Resomer polymers are available in different Lactide to Glycolide molar ratio and inherent viscosity, e.g., Resomer RG 502H, Resomer RG 502, Resomer RG 503H, Resomer RG 503, Resomer RG 504H, Resomer RG 504, Resomer RG 653H, Resomer RG 752H, Resomer RG 752, Resomer RG 753; first two digit in grade indicates molar ratio of lactide in polymer, H indicates acid terminated polymer, and grades without H indicate ester terminated polymer), PURASORB® and Lakeshore (These are also providing PLGAs in different molar ratio and viscosity grades), WAKO® (Low to medium viscosity Polymers are available). In one of the preferred embodiment mixture of PLGA and PLA is used as a biodegradable polymer.

The terminal groups of the poly(DL-lactide-co-glycolide) can either be hydroxyl, carboxyl, or ester depending upon the method of polymerization. Polycondensation of lactic or glycolic acid will provide a polymer with terminal hydroxyl and carboxyl groups. Ring-opening polymerization of the cyclic lactide or glycolide monomers with water, lactic acid, or glycolic acid will provide polymers with the same terminal groups. However, ring-opening of the cyclic monomers with a monofunctional alcohol such as methanol, ethanol, or 1-dodecanol will provide a polymer with one hydroxyl group and one ester terminal groups. Ring-opening polymerization of the cyclic monomers with a diol such as 1,6-hexanediol or polyethylene glycol will provide a polymer with only hydroxyl terminal groups. In the present invention, copolymer of lactic acid and glycolic acid (PLGA) could be either carboxyl terminated, hydroxyl terminated or ester terminated, preferably carboxyl terminated.

In the present invention copolymer of lactic acid and glycolic acid having a monomer ratio of lactic acid to glycolic acid in the range of about 50:50 to about 100:0 are used, depending upon the requirement. Preferably 85:15 PLGA, 75:25 PLGA, 70:30 PLGA, 65:35 PLGA, 50:50 PLGA and more preferably 50:50 PLGA is used.

Polymers such as PLGA are available in different molecular weight ranges e.g. starting from about average molecular weight of 1,000 to 200,000 Dalton or even more than that. In one of the embodiment PLGA is used having average molecular weight ranging from 4,000 to 60,000 Dalton, more preferably PLGA having average molecular weight ranging from 10,000 to 30,000 Dalton are used as a biodegradable polymer. Alternatively in one of the embodiment mixture of PLGA having average molecular weight from 10,000 to 30,000 Dalton and PLGA having average molecular weight from 4,000 to 6,000 Dalton is used.

The molecular weight of the polymer used can affect the rate of drug release. Under these conditions, as the molecular weight of the polymer increases, the rate of drug release from the system decreases. For relatively quick release of drug, low molecular weight polymers can be chosen to provide the desired release rate. However, in the present invention inventors have found that while using high molecular weight polymers, initial burst release was observed. Inventors have surprisingly found that initial burst release could be controlled by addition of low molecular weight biodegradable polymer.

The selection of type, molecular weight, and amount of biodegradable polymer for the composition generally depend upon the desired properties of the prolonged release implant. For example, the type, molecular weight, and amount of biodegradable polymer can influence the length of time up to which the goserelin acetate is released from the in-situ prolonged release implant. It has also been observed that the selection of mixture of different PLGAs, having different molecular weight in different ratios are critical in controlling the burst. Preferably PLGA having average molecular weight ranging from 4000 to 20000 Dalton is considered as low molecular weight polymer, 20000 to 40000 dalton is considered as medium molecular weight polymer and more than 40000 dalton is considered as high molecular weight polymer. Polymer concentration in the polymer solution is critical for the release of goserelin from in-situ implant as it is generally seen that more dilute the concentration, more readily the drug would releases and as the concentration get increase, release of drug get slow. The inventor of present invention have found that optimization of polymer concentration in polymer solution can produce the desired release of goserelin from in-situ implant.

The biodegradable polymer can be present in any suitable amount. The suitable biodegradable polymer is preferably present in an about 20 wt. % to about 80 wt. % of the composition, more preferably present in about 30 wt. % to about 50 wt. % of the composition.

Biocompatible organic solvent can be employed, provided that such solvent is miscible to dispersible in aqueous medium or body fluid. Such biocompatible organic solvent should be able to diffuse into body fluid so that the in-situ implant composition coagulates or solidifies to form solid implant. Further, such selected solvent should be compatible with the used biodegradable polymer. Examples of suitable organic solvents include organic solvents having an amide group, an ester group, a carbonate group, a ketone, an ether, a sulfonyl group, or a combination thereof.

Specifically, the biocompatible organic solvent can be used in the present invention are N-methyl-2-pyrrolidone (NMP), 2-pyrrolidone, propylene carbonate, ethylene carbonate, dimethyl carbonate, 2-ethyoxylyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate, acetone, methyl ethyl ketone, solketal, glycerol formal, glycofurol, dimethylformamide, dimethylacetamide, dimethylsulfoxide (DMSO), dimethylsulfone; tetrahydrofuran; epsilon-caprolactone, butyrolactone, caprolactam, N,N-dimethyl-m-toluamide, 1-dodecylazacycloheptan-2-one, benzyl alcohol, benzyl benzoate, triaetin or mixtures thereof. Preferred biocompatible organic solvent is N-methyl-2-pyrrolidone. In the present invention concentration of biocompatible organic solvent can be taken in the range of about 20% to about 80% by weight of the composition, more preferably in the range of about 50% to about 70% by weight of the composition. Surprisingly, in the present invention the inventors have found that combination of biocompatible organic solvents also helps in reducing the burst release, preferably combination of NMP with benzyl benzoate. The preferred range of benzyl benzoate is of about 10 to about 25% by weight of the composition.

The type and amount of biocompatible organic solvent present in the composition will typically depend upon the desired properties of the controlled release implant. For example, the type and amount of biocompatible organic solvent can influence the length of time in which the goserelin acetate is released from the controlled release implant.

In one of the embodiment, rate retarding agents can also be added to reduce the burst effect in the composition. Such retarding agents can be selected from the group comprising of ester of a mono, di or tricarboxylic acid, a polyhydroxy alcohol, a fatty acid, a fatty, acid ester, epoxidized oil, a sterol, a higher alkyl alcohol, and any mixture thereof.

In one of the embodiment of the present invention, goserelin solution can be prepared in a suitable solvent, which is then sterilized by suitable technique such as membrane filtration and lyophilized subsequently in a container, preferably in a syringe or vial.

In one of the preferred embodiment, goserelin acetate solution can be prepared in either acetic acid or in water which is sterilized by membrane filtration and lyophilized subsequently. Preferably goserelin acetate solution is prepared in water, sterilized by membrane filtration and lyophilized subsequently in a suitable container.

In one of the embodiment, suitable biodegradable polymer is dissolved in a suitable solvent, which is then sterilized by suitable technique such as membrane filtration and subsequently subjected to aseptic drying using suitable technique such as lyophilization or spray drying. Then the polymer can be mixed with sterilized biocompatible organic solvent & filled in to suitable container, preferably syringe or vial.

In one of the preferred embodiment, PLGA is dissolved in an acetic acid, which is then sterilized by membrane filtration technique and subsequently subjected to aseptic drying using suitable technique such as lyophilization or spray drying. Then the polymer is mixed with sterilized NMP & filled into suitable container, preferably syringe or vial.

It has been observed from the prior art that the viscosity of the mixture of biodegradable polymer in biocompatible organic solvent is too high and hence filtration through membrane filter becomes difficult. Surprisingly, in the present invention the inventors have found that dissolving biodegradable polymer in suitable solvent helps in filtration and solvent is then removed by lyophilization or spray drying, prior to mixing with biocompatible organic solvent and hence makes processing easy. For example, dissolving PLGA into acetone, acetic acid, chloroform, dichloromethane, ethyl acetate, ethyl formate, methyl ethyl ketone, methyl isobutyl ketone or suitable solvent, solution having lower viscosity and hence membrane filtration becomes easy.

In an alternative embodiment of the present invention, part of the biodegradable polymer can be added with goserelin solution and subsequently lyophilized in a suitable container, preferably syringe or vial, whereas the remaining part of the biodegradable polymer can be either mixed with the biocompatible organic solvent and sterilized separately by suitable technique and filled in the suitable container or remaining part of the biodegradable polymer can be processed as per above technique i.e. dissolving in solvent followed by sterilization, lyophilization, mixing with organic solvent and filling.

In an another embodiment of the present invention, goserelin solution is prepared in a suitable solvent, which is than sterilized by suitable technique such as membrane filtration and lyophilized subsequently and filled in the suitable container, preferably syringe or vial. Suitable biodegradable polymer is dissolved in a suitable solvent which is than sterilized by suitable technique such as membrane filtration and lyophilized subsequently. The strong acid is dissolved in a biocompatible organic solvent and sterilized by suitable technique & mixed with lyophilized polymer and filled in to suitable container, preferably syringe or vial.

The strong acids suitable for the present invention may be selected from, but not limited to, the group consisting of hydrochloric acid, hydrobromic acid, nitric acid, chromic acid, sulfuric acid, methanesulfonic acid, trifluoromethane sulfonic acid, trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, pamoic acid, perchloric acid, phosphoric acid, hydrogen iodide, acetic acid, trifluoroacetic acid, propionic acid, succinic acid, glycolic acid, stearic acid, lactic acid, malic acid, tartaric acid, citric acid, ascorbic acid, maleic acid, hydroxymaleic acid, phenylacetic acid, glutamic acid, benzoic acid, salicylic acid, mesylic acid, esylic acid, besylic acid, sulfanilic acid, 2-acetoxybenzoic acid, fumaric acid, toluenesulfonic acid, ethane disulfonic acid, oxalic acid, isethionic acid and the like.

Such strong acid when mixed with the drug is capable of forming different pharmaceutically acceptable salt having different solubility property than the original salt. Preferably in the present invention pamoic acid or methanesulfonic acid is used.

In the lyophilization of any solution primary drying is generally performed below glass transition temperature of the solution to obtain elegant porous cake. Surprisingly, in the present invention it has been found that the lyophilization of the solution of goserelin acetate or its mixture with biodegradable polymer in acetic acid and also of the aqueous solution of goserelin acetate, primary drying performed above glass transition temperature have given elegant porous cake.

In another embodiment, the present invention provides a kit which includes a first container and a second container. Preferably, the first container is a syringe or vial and the second container is a syringe or vial. The containers can be connected or separate.

One of the embodiment of present invention is a method of administration of composition of invention wherein prior to administration the content of the two containers are mixed together until the polymer/solvent solution and the goserelin are effectively mixed together and the prepared composition can then be injected through the needle into the body.

The amount of goserelin incorporated into the present composition depends upon the desired release profile, the concentration of goserelin required for a biological effect, and the length of time that the goserelin has to be released for treatment.

The goserelin or its pharmaceutically acceptable salts can be used in the present invention in amounts ranging from equivalent to about 1 mg to about 25 mg of goserelin base. Preferably the goserelin present in amounts ranging from equivalent to about 3.6 mg to about 21.6 mg of goserelin base.

Specifically, in one embodiment of the present invention, the composition can be used to formulate a one month delivery system of goserelin. Alternatively, in another embodiment of the present invention, the composition can be used to formulate a three month delivery system of goserelin or a six month delivery system of goserelin. In such an embodiment, the goserelin can preferably be present in about 0.5 wt. % to about 5 wt. % of the composition.

It has been observed that the time required to prepare a polymer solution in a biocompatible organic solvent is less when using lyophilized polymer as compared to polymer without processed under lyophillization.

The amount of composition to be administered will typically depend upon the desired properties of the prolonged release implant. For example, the amount of composition can influence the length of time in which the goserelin is released from the implant.

In one of the embodiment, the present invention also provides process for the preparation pharmaceutical composition capable of forming in-situ implant. The process includes mixing, in any order, a biodegradable polymer, a biocompatible organic solvent, and goserelin. These ingredients, their properties, and preferred amounts are as disclosed above.

There are various techniques available for the sterilization such as membrane filtration, gamma-irradiation, chemical sterilization etc. Effect of gamma irradiation on polymer molecular weight was also observed. When the polymer solution was subjected to gamma irradiation for sterilization, the polymer molecular weight decreases and eventually PDI increases. When the polymer solution was subjected to membrane filtration for sterilization, the polymer molecular weight almost remains constant and eventually PDI remain constant. In the present invention the biodegradable polymers and biocompatible organic solvents are preferably sterilized by membrane filtration or gamma-irradiation and more preferably by membrane filtration.

In one of the embodiment, present invention provides a general process for the preparation of composition capable of forming in-situ implant comprising:
1. Preparing goserelin solution in a suitable solvent, sterilizing the solution by membrane filtration and subsequent lyophilizing in a suitable container closure system;
2. Mixing biodegradable polymer and biocompatible organic solvent and sterilized into a suitable container closure system by suitable technique or aseptically mixed after sterilizing separately and filled into a suitable container closure system.

In another embodiment, present invention provides a process for the preparation of composition capable of forming in-situ implant comprising:
1. Preparing goserelin solution in suitable solvent, sterilizing the solution by membrane filtration and subsequent lyophilizing in a suitable container closure system;
2. Dissolving biodegradable polymer in a suitable solvent and sterilizing by membrane filtration technique and lyophilized in bulk;
3. Sterilizing biocompatible organic solvent separately by membrane filtration technique;

4. Mixing polymer and solvent of step 2 & 3 aseptically and filling in a suitable container closure system.

In another embodiment, present invention provides a process for the preparation of composition capable of forming in-situ implant comprising:
1. Preparing goserelin solution in suitable solvent, sterilizing the solution by membrane filtration and subsequent lyophilizing in a suitable container closure system;
2. Dissolving biodegradable polymer in a suitable solvent and sterilizing by membrane filtration technique and drying aseptically by spray drying;
3. Sterilizing biocompatible organic solvent separately by membrane filtration technique;
4. Mixing polymer and solvent of step 2 & 3 aseptically and filling in a suitable container closure system.

In one of the preferred embodiment, present invention provides a process for the preparation of composition capable of forming in-situ implant comprising:
1. Preparing goserelin acetate solution in water, sterilizing the solution by membrane filtration and subsequent lyophilizing in a suitable container in which primary drying is performed above glass transition temperature of the goserelin acetate solution;
2. Dissolving PLGA in an acetic acid and sterilizing the solution by membrane filtration technique and lyophilized;
3. Sterilizing NMP by membrane filtration technique;
4. Mixing polymer and solvent of step 2 & 3 aseptically and filling in a suitable container closure system.

In one of the embodiment, the present invention provides a method of treating cancer in a patient. The method includes administering to the patient in need of such treatment an effective amount of a composition of the present invention. Specifically, the cancer can be prostate cancer, endometriosis, as an endometrial-thinning agent prior to endometrial ablation for dysfunctional uterine bleeding, and in the palliative treatment of advanced breast cancer in pre- and perimenopausal women.

In another embodiment, present invention includes kit containing composition for in-situ implant comprising: (a) a first vial comprising a composition comprising a biodegradable polymer and a biocompatible organic solvent; wherein the biocompatible organic solvent is miscible to dispersible in aqueous medium or body fluid; and (b) a second vial comprising goserelin, preferably goserelin acetate in a lyophilized form.

In another embodiment, present invention includes kit containing composition for in-situ implant comprising: (a) a first vial comprising a composition comprising a biodegradable polymer and a biocompatible organic solvent characterized in that the biodegradable polymer is aseptically dried either by lyophilization or spray drying prior to mixing with biocompatible organic solvent; and (b) a second vial comprising goserelin, preferably goserelin acetate in a lyophilized form.

In another embodiment, present invention includes kit containing composition for in-situ implant comprising: (a) a first vial comprising a composition comprising a biodegradable polymer and goserelin; preferably goserelin acetate in a lyophilized form and (b) a second vial comprises a biocompatible organic solvent; wherein the biocompatible organic solvent is miscible to dispersible in aqueous medium or body fluid.

Pharmacodynamic Study

The composition as mentioned hereinafter in example 8 was subjected to pharmacodynamic study conducted in healthy male wistar rat to compare the effect with Zoladex®. An evaluation of pharmacodynamic profile of goserelin in-situ implant of present invention in comparison with Zoladex® depot was carried out in wistar rats. Implants, containing 3.6 mg of goserelin, were administered by subcutaneous route. Each group (N=15) was administered three doses of goserelin implants at an interval of 28 days. Blood samples were withdrawn at predefined time intervals for the measurement of testosterone levels.

|  | Serum Testosterone | | Castration Incidences (N = 15) | |
| --- | --- | --- | --- | --- |
|  | Goserelin in-situ implant (Example 8) | Zoladex 3.6 mg | Goserelin in-situ implant (Example 8) | Zoladex 3.6 mg |
| Day 1 | 8.30 | 10.68 | 0 | 0 |
| Day 4 | 1.38 | 1.01 | 3 | 4 |
| Day 8 | 0.46 | 0.33 | 13 | 12 |
| Day 16 | 0.47 | 0.24 | 11 | 14 |
| Day 20 | 0.43 | 0.28 | 10 | 14 |
| Day 24 | 0.66 | 0.48 | 8 | 10 |
| Day 29 | 0.78 | 0.60 | 5 | 10 |
| Day 36 | 0.87 | 0.65 | 4 | 8 |
| Day 43 | 0.76 | 0.57 | 4 | 10 |
| Day 50 | 0.20 | 0.15 | 15 | 15 |
| Day 57 | 0.15 | 0.12 | 15 | 15 |
| Day 60 | 0.24 | 0.19 | 14 | 15 |
| Day 64 | 0.31 | 0.32 | 15 | 13 |
| Day 68 | 0.39 | 0.31 | 14 | 14 |
| Day 72 | 0.43 | 0.34 | 13 | 14 |

Note:
Castration level: Testosterone Level below 0.5 ng/ml.

The invention will be further illustrated by the following Examples, however, without restricting its scope to these embodiments.

EXAMPLES

Example-1

Tg' (Glass transition temperature) of aqueous goserelin solution (100 mg/ml) was determined by DSC (Mettler). About 60 □l of sample was taken and cooled rapidly to −65° C. at 20° C./min. The sample was then heated slowly at 5° C./min to 15° C.

Observation: Onset of glass transition was observed at −56.4° C. and mid point was observed at −55.16° C. (Tg').

Example-2

Tg' of goserelin solution in acetic acid (100 mg/ml) was determined by DSC (Mettler). About 50 □l of sample was taken and cooled rapidly to −65° C. at 20° C./min. The sample was then heated slowly at 5° C./min to 15° C.

Observation: Onset of glass transition was observed at −56.4° C. and mid point was observed at −55.14° C. (Tg').

Example-3

| Ingredients | Example 3A | Example 3B |
| --- | --- | --- |
| Goserelin | 12 mg/ml | 12 mg/ml |
| Solvent | Purified water | Acetic acid |
| Fill volume | 0.5 ml | 0.5 ml |
| Vial | 2 ml clear | 2 ml clear |

Vials: 2 ml clear tubular glass vial (USP Type I).
Stopper: 13 mm double slotted grey bromo butyl rubber stopper.

For the example-3A & example-3B lyophilization was performed as per the lyophilization cycle mentioned below.

Lyophilization Cycle

| No | Stages | Temperature (° C.) | Pressure (mtorr) | Duration (Hr:min) |
|---|---|---|---|---|
| 1 | Freezing | | | |
| | 1 (Freezing) | −40 | | 6:00 |
| | Product Freeze Temp | −35 | | |
| | Vacuum set temp (Condenser temp) | −50 | | |
| | Vacuum required | | 300 | |
| | Vacuum stabilization time | | | 0:01 |

| | | Shelf Temp. (° C.) | Pressure (mtorr) | Duration (Hr:min) |
|---|---|---|---|---|
| 2 | Primary Drying | | | |
| | Step-1 | −30 | 262 | 8:00 |
| | Step-2 | −20 | 262 | 7:00 |
| | Step-3 | −10 | 262 | 6:00 |
| | Step-4 | 0 | 150 | 7:00 |
| | Step-5 | 10 | 150 | 6:00 |
| | Step-6 | 20 | 112 | 6:00 |
| 3 | Secondary Drying | 30 | 50 | 10:00 |
| | Total cycle time | | | 56:00:00 |

Observations: Good intact cake was obtained for both compositions.

Example-4

| Ingredients | Content |
|---|---|
| PLGA (50:50, 0.2 dl/g) | 40% |
| N-methyl-2-pyrrolidone (NMP) | 55% |
| Goserelin acetate | 3.6 mg |
| Mixture of PLGA 50:50 (0.2 dl/g) and NMP | 0.3 ml |

PLGA was dissolved in NMP to get polymer solution and the solution was sterilized by gamma-irradiation. The sterilized polymer solution was added to lyophilized goserelin and gently stirred to get uniform dispersion. Dispersion when injected subcutaneously into rats, solid implant was formed after some time in-situ.

Example 5 & 6

| Ingredients | Example 5 | Example 6 |
|---|---|---|
| Goserelin | 0.5-2% | 0.5-2% |
| PLGA (50:50, 0.2 dl/g) | 25-55% | 20-50% |
| PLGA (50:50, 0.09 dl/g) | — | 5-30% |
| N-methyl-2-pyrrolidone (NMP) | 45-70% | 40-70% |

Dissolve PLGA into acetic acid and filter through 0.22μ membrane filter. Lyophilize the filtered solution to get dried powder. Dissolve lyophilized PLGA in sterilized NMP with continuous stirring to get polymer solution. Fill the polymer solution in suitable container and closure.

Separately, dissolve goserelin in water for injection and filter through 0.22μ membrane filter. Fill the solution in suitable vials and lyophilize to get dried product.

Before use, add polymer solution into lyophilized goserelin and mix gently to get homogeneous dispersion.

Example-7

| Ingredients | Content |
|---|---|
| Goserelin | 0.5-2% |
| PLGA (50:50, 0.2 dl/g) | 25-55% |
| Benzyl benzoate | 5-30% |
| N-methyl-2-pyrrolidone (NMP) | 20-70% |

Dissolve PLGA into acetic acid and filter through 0.22μ membrane filter. Lyophilize the filtered solution to get dried powder. Dissolve lyophilized PLGA in sterilized mixture of NMP and Benzyl benzoate with continuous stirring to get polymer solution. Fill the polymer solution in suitable container and closure.

Separately, dissolve goserelin in water for injection and filter through 0.22μ membrane filter. Fill the solution in suitable vials and lyophilize to get dried product.

Before use, add polymer solution into lyophilized Goserelin and mix gently to get homogeneous dispersion.

Example-8

Preparation of In-Situ Implant of Goserelin Acetate

1. Preparation of Goserelin Acetate Vial Lyophilized

Aqueous solution of Goserelin was prepared by dissolving 1.2 g Goserelin in 100 ml WFI. Solution was filtered through 0.2μ PVDF membrane filter and 0.5 ml solution filled in 2 ml vials each. Vials were loaded into lyophilizer after closing partially with rubber closure and lyophilized.

2. Preparation of Lyophilized PLGA and Polymer Solution 2.5 g of PLGA 5050 (I.V. 0.18 dl/g) and 7.5 g of PLGA 5050 (I.V. 0.28 dl/g) were dissolved in acetic acid (volume 100 ml) and filtered through 0.2μ PVDF membrane filter. Solution was filled in 20 ml clear vial and lyophilized with primary drying at −30 to 20° C. for 47 hrs and secondary drying at 30° C. for 12 hrs. In each lyophilized vial 1.2 ml NMP (aseptically filtered) was added to yield polymer solution 3. Preparation of Reconstituted Formulation 0.5 ml polymer solution was withdrawn in syringe and injected in a vial of lyophilized Goserelin and allowed to mix. 0.3 ml of Reconstituted formulation was withdrawn in syringe to deliver 3.6 mg Goserelin.

| | |
|---|---|
| Goserelin | 3.6 mg |
| Polymer solution | 0.3 ml |
| 5050DLG2A . . . 10% w/w | |
| 5050DLG3A . . . 30% w/w | |
| NMP . . . 60% w/w | |

4. Dissolution Method 0.3 ml reconstituted formulation was injected in 0.3 ml PBS buffer pH 7.4 at temperature 39° C. and allowed implant to form. After 2 hrs, 50 ml media was added in the same flask and incubated at 39° C. for 28 days with complete media replacement at every 7 days. Samples were withdrawn at regular interval and analyzed for goserelin content using reversed phase HPLC method In Vitro Release Profile:

| Time (Days) | Mean % release (N = 3) |
|---|---|
| 0.08 | 5.4 |
| 1 | 20.1 |
| 3 | 34.6 |
| 7 | 37.3 |
| 9 | 40.8 |
| 12 | 48.9 |
| 14 | 56.4 |
| 17 | 61.8 |
| 21 | 64.0 |
| 24 | 71.2 |
| 28 | 73.1 |

Example-9

Preparation of In-Situ Implant of Goserelin Acetate

| Goserelin acetate equivalent to | 3.6 mg Goserelin |
|---|---|
| Polymer solution | 0.3 ml |
| Purasorb 5002A . . . 40% | |
| Wako 5005 . . . 5% | |
| NMP . . . 55% | |

Procedure:
1. PLGA was dissolved in N-methylpyrrolidone to achieve desired concentration.
2. PLGA solution was filled in vials and sterilized by gamma radiation at 25 KGy. (Time for solution preparation—60 to 150 min)
3. Polymer solution was added in lyophilized Goserelin for reconstitution.

Example-10

Preparation of In-Situ Implant of Goserelin Acetate

Procedure:
1. Dissolved PLGA in glacial acetic acid at concentration 10% w/v.
2. Filtered the prepared solution through PVDF filter membrane with 0.22μ, pore size.
3. Filtered solution was filled in container (vials) and lyophilize.
4. Lyophilized PLGA was dissolved in N-methylpyrrolidone to achieve desired concentration. (Time for Solution preparation—15 to 20 min)
5. Polymer solution was added in a vial containing lyophilized Goserelin for reconstitution.

| Goserelin acetate equivalent to | 3.6 mg Goserelin |
|---|---|
| Polymer solution | 0.3 ml |
| Purasorb 5002A . . . 40% | |
| Wako 5005 . . . 5% | |
| NMP . . . 55% | |

Example-11

Preparation of In-Situ Implant of Goserelin Acetate (for Three Months Profile)

| Goserelin acetate equivalent to | 10.8 mg Goserelin |
|---|---|
| Polymer solution | 0.4 ml |
| Purasorb 7507 . . . (30% w/w) | |
| Triacetin . . . (5% w/w) | |
| NMP . . . (65% w/w) | |
| Injection wt/vol | 400 mg |

*Each 400 mg contains Goserelin acetate equivalent to 10.8 mg Goserelin

Procedure:
1. PLGA was dissolved in N-methylpyrrolidone to achieve desired concentration. (Time for solution preparation—60 to 150 min)
2. PLGA solution was filled in vials and sterilized by gamma radiation at 25 KGy.
3. Polymer solution was added in lyophilized Goserelin for reconstitution.

In Vitro Release Profile:
(Mean calculated on the basis of average of three different in-situ implants of the same formulation)

| Time (days) | Mean % Release (N = 3) |
|---|---|
| 0 | 0 |
| 0.08 | 5.8 |
| 1 | 22.5 |
| 7 | 41.5 |
| 14 | 49.2 |
| 21 | 52.2 |
| 28 | 54.0 |
| 35 | 55.2 |
| 44 | 56.3 |
| 56 | 72.7 |
| 68 | 77.4 |
| 70 | 79.0 |
| 82 | 79.5 |

Example-12

Evaluation of Burst Release in Rats

Goserelin dose: 3.6 mg/Rat
Route of administration: Subcutaneous
Injection volume: 0.3 ml
Number of animals: 3
Sampling Points: 2, 6 and 24 hrs

| Formulation Composition | $C_{max}$ (ng/ml) | Burst Index |
|---|---|---|
| PLGA 5050 (I.V. 0.21 dl/g) 40% NMP (Pharmasolve) 60% | 1310.4 | 1.0 |
| PLGA 5050 (I.V. 0.21 dl/g) 40% PLGA 5050 (I.V. 0.09 dl/g) 5% NMP (Pharmasolve) 55% | 841.1 | 0.6418536 |
| PLGA 5050 (I.V. 0.21 dl/g) 40% PLGA 5050 (I.V. 0.09 dl/g) 5% Benzyl benzoate 15% NMP (Pharmasolve) 40% | 248.8 | 0.1898657 |

1. Addition of low molecular weight polymer reduces $C_{max}$ by 40% as compared to high molecular weight polymer alone.

2. Combination of polymers & addition of non-polar solvent like benzyl benzoate in formulation caused 80% reduction in $C_{max}$ as compared to single polymer and single solvent system.

Example-13

3 g of PLGA 5050 (I.V. 0.3 dl/g) dissolved in 30 ml of Acetone and filtered through 0.22☐ membrane filter. The filtered solution was subsequently spray dried in mini-spray dryer with inert loop. Nitrogen was used as inert gas and other process conditions were Inlet air temperature: 75° C.
Outlet air temperature: 40-45° C.
Air flow: 35-37 m³/hr
Spray rate: 3 ml/min The inherent viscosity of dried polymer was determined. There was no change observed in the inherent viscosity indicating polymer remains intact during the process.

Example-14

Solution of PLGA 5050 (I.V. 0.3 dl/g) was prepared in the solvent mentioned in table below and stability of PLGA was studied at room temperature by determining the viscosity of polymer solution. Viscosity of solution was determined using Brookfield CAP2000+ viscometer.

| | Viscosity (cps) of polymer solution Solvent | | | | |
|---|---|---|---|---|---|
| Time | Acetic acid | Acetone | DCM | Ethyl acetate | MEK |
| | Polymer Concentration | | | | |
| points | 20% w/w | 25% w/w | 25% w/w | 25% w/w | 25% w/w |
| Initial | 62.5 | 49.65 | 40.95 | 76.9 | 84.9 |
| 1 hr | 62.6 | 46.1 | 43.05 | 79.6 | 74.45 |
| 2 hr | 61.85 | 47.25 | 46.25 | 75.4 | 69.55 |
| 3 hr | 61.9 | 47.85 | 39.75 | 78.3 | 72.4 |
| 4 hr | 62.4 | 47.8 | 38 | 75.45 | 81.7 |
| 5 hr | 63.7 | 52.05 | 39.95 | 81.6 | 81.1 |

There was no significant change in the viscosities of polymer solution indicating no degradation of polymer during this time interval.

The invention claimed is:

1. A pharmaceutical product comprised of components capable of forming an in-situ implant comprising:
   a) a first component comprised of goserelin acetate in lyophilized powder form;
   b) a second component comprised of a solution comprising
      a mixture of at least a high or medium weight average molecular weight biodegradable polymer and a low weight average molecular weight biodegradable polymer, and
      a biocompatible organic solvent present in 20% to 80% by weight of the composition;
   wherein the low weight average molecular weight biodegradable polymer has a weight average molecular weight of from 4,000 to 20,000 Da wherein the in-situ implant comprised of a mixture of the first and second components has an in vivo burst index that is less than an in situ implant comprised of goserelin acetate and at least a high or medium weight average molecular weight biodegradable polymer.

2. The pharmaceutical product as claimed in claim 1, wherein the biodegradable polymers comprised within the mixture are selected from the group consisting of polylactides, polyglycolides, copolymer of lactic acid and glycolic acid, polycaprolactones, polydioxannones, polycarbonates, polyhydroxybutyrates, polyalkyene oxalates, polyanhydrides, polyamides, polyesteramides, polyurethanes, polyacetals, polyketals, polyorthocarbonates, polyphosphazenes, polyhydroxyvalerates, polyalkylene succinates, poly(malic acid), poly(amino acids), chitin, chitosan, polyorthoesters, and copolymers, terpolymers, block copolymers, branched copolymers, and mixtures thereof.

3. The pharmaceutical product as claimed in claim 2, wherein the biodegradable polymer is selected from the group consisting of polylactides, polyglycolides, copolymer of lactic acid and glycolic acid, polycaprolactones, and mixtures thereof.

4. The pharmaceutical product as claimed in claim 3, wherein the biodegradable polymer is copolymer of lactic acid and glycolic acid.

5. The pharmaceutical product as claimed in claim 4, wherein the copolymer of lactic acid and glycolic acid has a carboxyl terminal group or ester terminal group.

6. The pharmaceutical product as claimed in claim 5, wherein the copolymer of lactic acid and glycolic acid has a carboxyl terminal group.

7. The pharmaceutical product as claimed in claim 1, wherein the amount of biodegradable polymer is between about 20% to about 80% by weight of the composition.

8. The pharmaceutical product as claimed in claim 1, wherein the amount of biodegradable polymer is between about 30% to about 50% by weight of the composition.

9. The pharmaceutical product as claimed in claim 1, wherein the biocompatible organic solvent is selected from the group consisting of N-methyl-2-pyrrolidone, 2-pyrrolidone, propylene carbonate, ethylene carbonate, dimethyl carbonate, 2-ethyoxylyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate, acetone, methyl ethyl ketone, solketal, glycerol formal, glycofurol, dimethylformamide, dimethylacetamide, dimethylsulfoxide, dimethylsulfone; tetrahydrofuran; epsilon-caprolactone, butyrolactone, caprolactam, N,N-dimethyl-m-toluamide, 1-dodecylazacycloheptan-2-one, benzyl alcohol, benzyl benzoate, triacetin, and mixtures thereof.

10. The pharmaceutical product as claimed in claim 9, wherein the biocompatible organic solvent is N-methyl-2-pyrrolidone.

11. The pharmaceutical product as claimed in claim 9, wherein the biocompatible organic solvent is a mixture of N-methyl-2-pyrrolidone and benzyl benzoate.

12. The pharmaceutical product as claimed in claim 1, wherein the biocompatible organic solvent is present in about 50% to about 70% by weight of the composition.

13. A process for the preparation of a pharmaceutical product capable of forming an in-situ implant comprising:
   1) preparing a goserelin acetate solution in a suitable solvent, sterilizing the solution by a suitable technique, and subsequently lyophilizing in a first suitable container;
   2) separately sterilizing a mixture of at least a high or medium weight average molecular weight biodegradable polymer and a low weight average molecular weight biodegradable polymer and biocompatible organic solvent by a suitable technique, and filling the mixture into a second suitable container, wherein the low weight average molecular weight biodegradable polymer of said mixture has a weight average molecular weight of from 4000 to 20000 Da.

14. A process for the preparation of a pharmaceutical product capable of forming an in-situ implant comprising:
1) preparing a goserelin acetate solution in a suitable solvent, sterilizing the solution by membrane filtration and subsequently lyophilizing in a first suitable container;
2) dissolving a mixture of at least a high or medium weight average molecular weight biodegradable polymer and a low weight average molecular weight biodegradable polymer in a suitable solvent and sterilizing by membrane filtration technique, and lyophilizing;
3) sterilizing separately a biocompatible organic solvent by a membrane filtration technique;
4) mixing the polymer and the solvent of step 2) and step 3 and filling in a second suitable container,
wherein the low weight average molecular weight biodegradable polymer of said mixture has a weight average molecular weight of from 4,000 to 20,000 Da.

15. A kit containing a composition for an in-situ implant comprising
(a) a first vial comprising a composition comprising:
i. a mixture of at least a high or medium weight average molecular weight biodegradable polymer and a low weight average molecular weight biodegradable polymer; and
ii. a biocompatible organic solvent present in 20% to 80% by weight of the composition; and
(b) a second vial comprising lyophilized goserelin acetate;
wherein the low weight average molecular weight biodegradable polymer of said mixture has a weight average molecular weight of from 4,000 to 20,000 Da wherein the in-situ implant comprised of a mixture of the first and second components has an in vivo burst index that is less than an in situ implant comprised of goserelin acetate and at least a high or medium weight average molecular weight biodegradable polymer.

16. The pharmaceutical product as claimed in claim 1 for once a month administration.

17. The pharmaceutical product as claimed in claim 1 for once in three months administration.

18. The pharmaceutical product as claimed in claim 1 for once in two months administration.

19. The pharmaceutical product as claimed in claim 1, wherein the mixture of biodegradable polymers is comprised of a first polymer having a weight average molecular weight from 20,000 to 40,000 Da and a second polymer having a weight average molecular weight from 4,000 to 20,000 Da.

20. The pharmaceutical product as claimed in claim 19, wherein said first polymer and second polymer are a copolymer of lactic acid and glycolic acid.

* * * * *